(12) United States Patent
Zhang et al.

(10) Patent No.: US 7,157,096 B2
(45) Date of Patent: Jan. 2, 2007

(54) COATINGS, COATED ARTICLES AND METHODS OF MANUFACTURE THEREOF

(75) Inventors: Zongtao Zhang, Unionville, CT (US); Tongsan D. Xiao, Willington, CT (US)

(73) Assignee: Inframat Corporation, Farminton, CT (US)

( * ) Notice: Subject to any disclaimer, the term of this patent is extended or adjusted under 35 U.S.C. 154(b) by 443 days.

(21) Appl. No.: 10/270,092

(22) Filed: Oct. 14, 2002

(65) Prior Publication Data

US 2003/0099762 A1   May 29, 2003

Related U.S. Application Data

(60) Provisional application No. 60/328,742, filed on Oct. 12, 2001.

(51) Int. Cl.
*A61F 13/00* (2006.01)
*A61F 2/00* (2006.01)
*A61K 9/14* (2006.01)

(52) U.S. Cl. .................. 424/422; 424/423; 424/489

(58) Field of Classification Search .................. 424/422
See application file for complete search history.

(56) References Cited

U.S. PATENT DOCUMENTS

| | | | |
|---|---|---|---|
| 4,675,189 A * | 6/1987 | Kent et al. .................. 424/490 |
| 5,077,132 A * | 12/1991 | Maruno et al. .............. 428/426 |
| 5,162,430 A | 11/1992 | Rhee et al. ................. 525/54.1 |
| 5,441,536 A | 8/1995 | Aoki et al. ................. 427/2.27 |
| 5,478,237 A | 12/1995 | Ishizawa .................. 433/201.1 |
| 5,730,598 A | 3/1998 | Story et al. ............... 433/201.1 |
| 5,763,092 A | 6/1998 | Lee et al. .................... 428/469 |
| 6,207,218 B1 * | 3/2001 | Layrolle et al. ........... 427/2.27 |
| 6,280,789 B1 | 8/2001 | Rey et al. .................. 427/2.27 |
| 6,432,437 B1 | 8/2002 | Hubbard .................... 424/424 |
| 2002/0076528 A1 | 6/2002 | Tomsia et al. .............. 428/195 |

FOREIGN PATENT DOCUMENTS

| | | |
|---|---|---|
| DE | 40 20 598 A1 | 1/1991 |
| DE | 40 32 570 A1 | 4/1992 |
| EP | 0 447 744 A2 | 1/1991 |

OTHER PUBLICATIONS

Kurzweg, H., et al. "Development of plasma-sprayed bioceramic coatings with bond coats based on titania and zirconia", Biomaterials, Elsevier Science Publishers BV., Barking, GB, vol. 19, No. 16, Aug. 1998, pp. 1507-1511, ISSN 0142-9612.

(Continued)

*Primary Examiner*—Carlos A. Azpuru
*Assistant Examiner*—David Vanik
(74) *Attorney, Agent, or Firm*—Cantor Colburn LLP

(57) ABSTRACT

A multi-layer coating is particularly useful for the coating of implants such as orthopedic and dental implants, particularly metallic implants. The first layer comprises a bond coating of a dense material insoluble and inert in body fluids. The second layer comprises apatite and a binder. The first layer protects the metallic implants from corrosion, apatite dissolution, and interfacial reaction with apatite and the binder. The apatite in the second layer is a bioactive agent that can osteobond to tissue. The binder allows adjustment of the thermal expansion coefficient between the coating and the metallic substrate. This multi-layer coating has both high bond strength to implants and excellent bioactivity with the surrounding body tissue.

7 Claims, 8 Drawing Sheets

OTHER PUBLICATIONS

International Search Report, International Appln. No. PCT/US02/33029, International filing date Oct. 14, 2002; Date of mailing Sep. 10, 2003.

Gomez-Vega, J. M., et al.; "Glass-based coatings for titanium implant alloys"; *J. Biomaterials Res.*, vol. 46, 549-559, 1999.

Han, Y. et al; "Characterization and stability of hydroxyapatite coatings prepared by an electrodeposition and alkaline-tretment process"; *J. Biomed Mater. Res.* vol. 54, No. 1, 96-101 (2000).

Sousa, S. R., et al.; "Effect of hydroxyapatite thickenss on metal ion relase from Ti6A14V substrates"; Biomaterials vol. 17, No. 4, 397-404 (1996).

Sun, L., et al.; "Material Fundamentals and Clinical Performance of Plasma-Sprayed Hydroxyapatite Coatings: A Review"; J. Biomed. Mat. Res. 58, 570-592 (2001).

Wei, M., et al.; "Electrophoretic Deposition of Hydroxyapatite Coatings on Metal Substrates: A Nanoparticulate Dual-Coating Approach"; Journal of Sol-Gel Science and Technology 21, 39-48, 2001.

Wei, M., et al.; "Interfacial bond strength of electrophoretically deposited hydroxyapatite coatings on metals"; Journal of Materials Science, Materials in Medicine 10; 401-409 (1999).

Yang, C. Y., et al.; "Bond degradation at the plasma-sprayed HA coating/Ti-B11-4V alloy intervace: an *in vitro* study"; *Journal of Materials Science: Materials in Medicine 6*, 258-265 (1995).

Zhitomirsky, I. et al.; "Electrophoretic deposition of hydroxyapatite"; *Journal of Materials Science Materials in Medicine 8* (4): 213-219, (1997).

J.M. Gomez-Vega et al., "Bioactive Glass-Mesoporous Silica Coatings on Ti6A14V Through Enameling and Triblock-copolymer-templated sol-gel Processing", J. Biomedical Materials Research 56: 382-389; Mar. 2, 2001.

S.R. Sousa et al., Effect of Hydroxyapatite Thickness on Metal Ion Release from Ti6A14V Substrates, Biomaterials 1996, vol. 17, No. 4, pp. 397-404.

* cited by examiner

COATINGS, COATED ARTICLES AND METHODS OF MANUFACTURE THEREOF

CROSS REFERENCE TO RELATED APPLICATIONS

This application claims the benefit of U.S. Provisional Patent Application Ser. No. 60/328,742 filed Oct. 12, 2001, which is fully incorporated herein by reference.

STATEMENT REGARDING FEDERALLY SPONSORED RESEARCH & DEVELOPMENT

This invention was made with government support under Grant No. NIH 1R43AR47278-02 awarded by The United States National Institute of Health. The United States Government has certain rights to this invention.

BACKGROUND

This disclosure relates to apatite materials, and in particular to coatings comprising apatite.

Synthetic apatites, including hydroxyapatite (HA), $Ca_{10}(PO_4)_6(OH)_2$, fluorapatite $Ca_{10}(PO_4)_6F_2$, or hydroxyfluorapatite $Ca_{10}(PO_4)_6(OH)_{2-x}F_x$ (x<1) have a similar composition to biological apatites $(Ca_{10-x}(HPO_4)_x(OH)_{2-x})$ principle components of hard tissues such as bone. Due at least in part to their excellent osteoconductivity, apatites have been used as a coating on metallic implants or prostheses (i.e., prosthetic hips) for biological fixation. Such an apatite coating has two interfaces, one with the tissue of the subject receiving the implant and one with the implant itself. The benefits of apatite coatings, particularly in early stage fixation, include decreased fibrous tissue growth near implant surface, a decrease in pain at the site of implantation, and increased bone or other favorable tissue growth onto the surface of the apatite coated metal implant.

While apatite coatings can have positive interactions with bone and tissue, the apatite-implant interface can be a source of failure. In *Biomaterials* 17: 397–404, 1996, it has been reported that the failure of apatite-coated implants is due at least in part to the intrinsic properties of apatite and metallic implants, including dissolution of amorphous apatite in body fluids, thermal expansion mismatch between apatite and the metallic substrate, and corrosion at the metal-coating interface during the service lifetime of the implant. While crystalline apatite, particularly crystalline hydroxyapatite, is relatively insoluble in body fluids, amorphous apatite and soluble impurities such as calcium phosphates (i.e., $Ca_3(PO_4)_2$, $Ca_4P_2O_9$) and CaO can dissolve into body fluids, leading to delaminated apatite layers and cracks in the coating. Cracks can also result from the large thermal expansion coefficient difference between the apatite and the metallic substrate. For instance, hydroxyapatite has a thermal expansion coefficient of $\alpha_{HA}=13.3\times10^{-6}/°$ C. and metallic alloys such as Ti6Al4V have a thermal expansion coefficient of $\alpha_{Ti\ alloy}=10.3\times10^{-6}/°$ C.

Once formed, individual cracks in the apatite-implant interface can lead to the formation of connective cracks. Cracks in the apatite-implant interface, particularly connective cracks, can allow the migration of body fluids. This fluid migration can corrode a titanium alloy substrate, thereby generating a high concentration of protons ($H^+$) at the apatite-implant interface (Eq. 1). The concentrated $H^+$ can dissolve the apatite coating upon contact at the apatite/Ti interface (Eq. 2), resulting in failure of implanted prostheses.

$$Ti+2H_2O \rightarrow TiO_2+4H^++4e^- \quad (1)$$

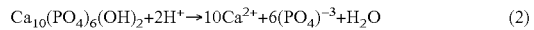

$$Ca_{10}(PO_4)_6(OH)_2+2H^+ \rightarrow 10Ca^{2+}+6(PO_4)^{-3}+H_2O \quad (2)$$

Because there is little circulation of body fluid at the interface local area, reactions (1) and (2) can occur continuously, until the apatite/Ti interface is nearly or completely separated and large interconnected cracks are formed. When these large cracks are wetted by the surrounding body fluid, circulation of the body fluid will quickly neutralize the local protons and increase the pH to it normal biological level. Once the pH is no longer acidic, the apatite dissolution will cease; however, by this time the apatite-implant interface will have been significantly degraded.

There thus remains a need for improved apatite containing coatings for metal substrates such as prostheses or implants.

SUMMARY

The above-described drawbacks and disadvantages are alleviated by a coating for an implant, comprising a first layer having a first thermal expansion coefficient and comprising a material selected from the group consisting of oxide compounds, nitride compounds, boride compounds, carbide compounds, and mixtures of two or more of the foregoing materials; and a second layer disposed on the first layer having a second thermal expansion coefficient and comprising an apatite having greater than about 90% crystallinity and a binder inert in body fluids, wherein the difference between the first and second thermal expansion coefficients is less than or equal to about $1\times10^{-6}/°$ C.

Further disclosed is a coated implant comprising a first layer having a first thermal expansion coefficient and a first side disposed on the implant and a second side disposed on a second layer, wherein the first layer comprises a material selected from the group consisting of oxide compounds, nitride compounds, boride compounds, carbide compounds, and mixtures of two or more of the foregoing materials; and a second layer having a second thermal expansion coefficient and a first side disposed adjacent the first layer, wherein the second layer comprises an apatite having greater than about 90% crystallinity and a binder that is inert in body fluids; and further wherein the difference between first and second thermal expansion coefficient is less than or equal to about $1\times10^{-6}/°$ C.

Further disclosed herein is a method of making a coated implant, comprising depositing a first layer on a metallic substrate, wherein the first layer comprises a material selected from the group consisting of oxide compounds, nitride compounds, boride compounds, carbide compounds, and mixtures of two or more of the foregoing materials; depositing a slurry comprising an apatite having greater than about 90% crystallinity and a binder that is inert in body fluids on the first layer to form a green coating; and sintering the green coating to form a second layer.

BRIEF DESCRIPTION OF THE DRAWINGS

Referring now to the drawings.

DETAILED DESCRIPTION OF THE PREFERRED EMBODIMENTS

Figure 1:
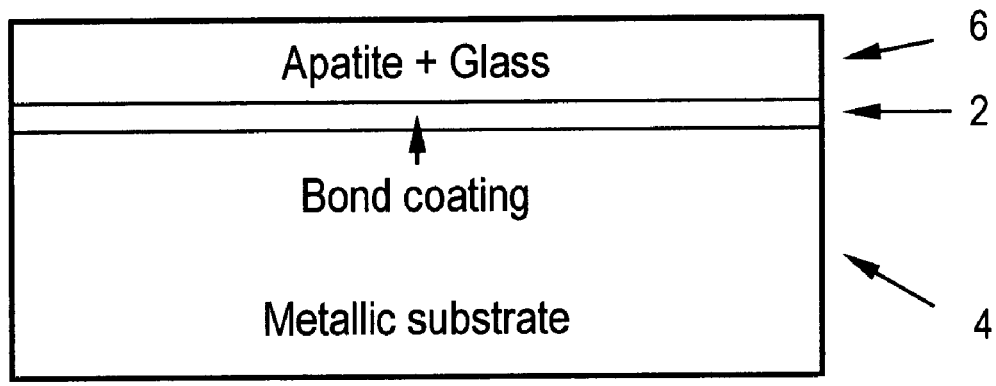
FIG. 1 shows a schematic diagram of one embodiment of a multi-layer coated article.

One reported approach to apatite coatings for implants involves the use of apatite composites coated directly onto an implant. Such composites are compositional gradients of apatite-bioglass composites. The function of the bioglass in these composites is to adjust the thermal expansion coefficient of the hydroxyapatite-bioglass composite to that of the metallic substrate and to provide additional bioactvity. However, the gradient apatite-bioglass composite coatings can experience interfacial reactions (3) and (4) at the bioglass/Ti interface.

$$Ti + 2SiO_2 \rightarrow TiSi_2 + 2O_2 \quad (3)$$

$$5Ti + 3SiO_2 \rightarrow Ti_5Si_3 + 3O_2 \quad (4)$$

The oxygen produced in the reactions can form large bubbles that decrease the interfacial bond strength. Additionally cracking can occur in the presence of body fluid and the cracks can extend rapidly due to the solubility of the bioglass in body fluids. The quality of the coating is sensitive to process parameters.

The coating disclosed herein is a multi-layer coating that is particularly useful as a coating for implants or prostheses, particularly on Ti, Ti6Al4V, CrCoMo, stainless steel alloys, and the like. As used herein, the implant or prosthesis may also be referred to as a metallic substrate or substrate for the coating. The first layer of the coating is a dense layer comprising a material that is insoluble in body fluids such as oxide compounds, nitride compounds, boride compounds, carbide compounds and mixtures of the foregoing materials. The first side of the first layer is disposed on the metal substrate (i.e., the prosthesis). The second side of the first layer is disposed on a first side of a second layer. The second layer of the coating is a composite comprising apatite and a binder that is insoluble in body fluids. The binder insoluble in body fluids can be a glass, such as, for example, medical glass having a high $SiO_2$ concentration (i.e., greater than 67.8%). Preferably, the apatite in the apatite-binder composite is present in a gradient perpendicular to the implant surface, wherein the apatite concentration at the side near the second side of the second layer (the tissue interface) is greater than that at the first side of the second layer (the prosthesis interface). The second layer is preferably about 5 micrometers to about 100 micrometers thick. There are several advantages to the disclosed multi-layer coating. The use of a first layer or dense coating layer allows separation of the second layer and the metallic implant, thus inhibiting the reaction of the apatite or the glass in the second layer with the metallic substrate. The use of an insoluble binder in the apatite-containing layer allows the adjustment of the thermal expansion coefficient of the coating, thus reducing or eliminating delamination due thermal expansion coefficient mismatch between the first and second layers and the substrate. The multi-layer coatings thus can have good bioreactivity with tissue as well as good adhesion to each other and to the metallic substrate.

Figure 2:
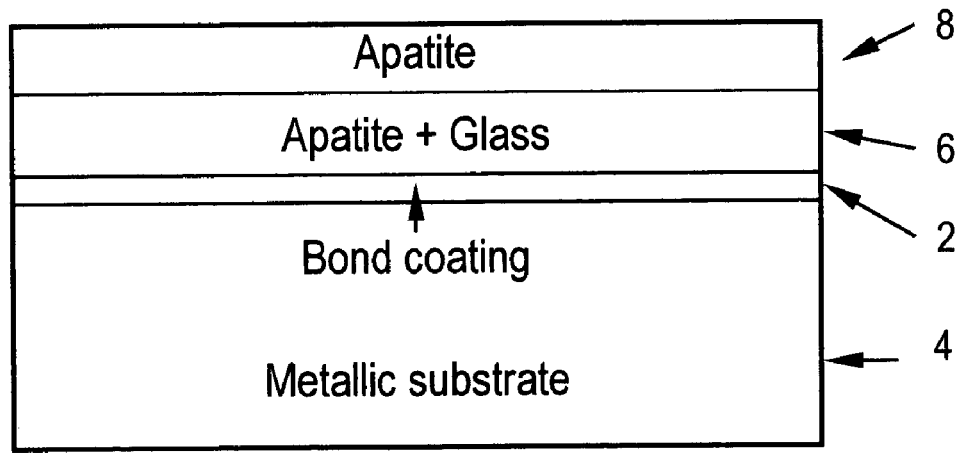
FIG. 2 shows schematic diagram of another embodiment of a multi-layer coated article.

Exemplary multi-layer coatings are shown in FIGS. 1 and 2. The first layer 2 is a dense layer comprising a compound insoluble in body fluids that is disposed on a metallic substrate 4. The second layer 6 is an apatite and an insoluble glass mixture with pure or nearly pure apatite on the top surface (i.e., adjacent the tissue interface). The optional third layer 8 disposed on the second layer in FIG. 2 comprises hydroxyapatite.

The first layer functions as a reaction barrier between the second layer and the metal substrate. The second layer supplies bioactivity for acceleration of bone growth on the implant surface. The optional third layer provides additional bioactivity. The multi-layer structure maximizes biocompatibility and interfacial bond strength.

The first layer comprises a compound insoluble in body fluid. As used herein, body fluid refers to a physiological fluid in a mammal, particularly a fluid that could come into contact with a prosthesis. Body fluid includes, for example, synovial fluid, blood, cerebrospinal fluid, saliva, and the like. Synovial fluid, for example, is an aqueous solution comprising several organic compounds, proteins, and chloride salts, phosphate salts, and sulfate salts of metals such as calcium, magnesium, potassium, and sodium. Exemplary mammals include, for example, humans, dogs, cats, horses, and the like.

The material insoluble in body fluid can be selected from the group consisting of oxide compounds, nitride compounds, carbide compounds, boride compounds, and compositions comprising one or more of the foregoing oxide compounds, carbide compounds, nitride compounds and boride compounds. Exemplary oxide compounds include, but are not limited to, $Al_2O_3$, $Fe_2O_3$, $Y_2O_3$, $Cr_2O_3$, $MnO_2$, $TiO_2$, $SiO_2$, $ZrO_2$, $HfO_2$, and combinations of the foregoing oxide compounds. Exemplary nitride compounds include, but are not limited to, TiN, CrN, ZrN, TiON, TiAlON and combinations of the foregoing nitride compounds. Exemplary carbide compounds include, but are not limited to, TiC, CrC, ZrC, TiCN, TiAlCN and combinations of the foregoing carbide compounds. Exemplary boride compounds include, but are not limited to, TiB$_2$, CrB, ZrB$_2$ and combinations of the foregoing boride compounds. Preferably the first layer comprises a nitride compound. More preferably, the first layer comprises titanium nitride (TiN), zirconium nitride (ZrN), chromium nitride (CrN), aluminum titanium nitride (TiAlN or AlTiN), as well as combinations comprising one or more of the foregoing nitride compounds. The nitride compounds are biocompatible and relatively resistant to body fluid corrosion, but have different oxidation temperatures, which are listed on Table 1. The higher the oxidation temperature, the better the corrosion resistance.

TABLE 1

| Nitride coatings characteristics | | | | |
| --- | --- | --- | --- | --- |
| | TiN | ZrN | CrN | TiAlN |
| Biocompatibility | Excellent | Excellent | Excellent | Excellent |
| Resistant corrosion | Yes | Yes | Yes | Yes |
| Oxidation Temp. | 500° C. | 500/600° C. | 700° C. | 800° C. |

Generally, the material employed in the dense fist layer is chosen so that it has a thermal expansion coefficient that differs from the thermal expansion coefficient of the substrate (i.e., implant) by less than or equal to about $1\times10^{-6}/°$ C. The thickness of the first layer is preferably about 0.5 micrometer to about 10.0 micrometers thick. If the first layer is less than about 0.5 micrometer thick, the layer may not be thick enough to protect the implant from corrosion and provide a diffusion barrier. If the layer is more than about 10.0 micrometers, the layer could become separated from the implant due to large residual stress after the coating processes.

The first layer provides a dense layer that functions as a corrosion barrier that can reduce corrosion of implants in body fluid. Implants made of titanium, titanium alloy (Ti6Al4V), stainless steel, and cobalt-chromium alloy can corrode in body fluid. When these metals corrode, an irreversible porous surface layer of oxides is formed. The porous oxides generate protons (H$^+$ in solution) which promote dissolution of apatite, and consequently the apatite-implant interface can be subject to failure, as indicated in Equations (1) and (2). While a porous oxide film can promote implant failure, a dense layer (i.e., of oxide, nitride, boride and/or carbide compounds) can protect the implant.

A first layer comprising, for example, a nitride compound, exhibits much higher corrosion resistance than the pure metal, so it can protect the metal implants. Even if other layers of the multi-layer coating have flaws that allow the penetration of body fluids, the first layer can provide a barrier to reduce the contact of body fluid with the metal implants. The first layer, for example, TiN, may be corroded in body fluid in the form of reaction (5), according to thermodynamic calculations. This nitride corrosion produces ammonium ions, which make the local pH more basic at the apatite-titanium nitride interface area. As a result, the apatite crystals remain stable. Therefore, the problem of weak interfacial bonding between hydroxyapatite and the metal implant during long term service can be ameliorated using a dense first layer in contact with the implant.

$$TiN + 2H_2O \rightarrow TiO_2 + NH_4^{+1} + e^- \quad (5)$$

The first layer also provides a reaction barrier that can reduce or eliminate reaction between the metallic implant and the components of the second layer of the coating, the apatite and the binder, i.e., glass. Implants can be made of titanium alloy (Ti6Al4V), stainless steel, and cobalt-chromium alloy which are active metals, i.e., metals which can easily react with the silica in the glass (during the subsequent sintering process) to produce titanium silicide and oxygen. As discussed above, the oxygen can form gas bubbles at the glass/Ti alloy interface area, which are detrimental to the interfacial bonding. The coating of a dense first layer such as TiN on a metal implant reduces the reactions that can occur between the metal alloy and other layers.

The first layer can also supply metallurgical bonding at its interfaces with both the implant and the second layer. The chemical potential gradient differences across the interfaces can set up counter current diffusion across the interfaces. Such diffusion should occur, albeit to different extents, with nitride, oxide, boride and carbide compounds. When atoms from the first layer, for example, diffuse into the metallic implant surface under sintering conditions, a metallurgical bond can be formed. For example, at sintering temperatures at about 900° C., nitrogen atoms from a TiN first layer can diffuse into the Ti6Al4V alloy, and Al as well as V can diffuse from the Ti6Al4V substrate into the TiN.

Further, when sintering is performed in the presence of oxygen, chemical reactions can occur at the interfaces of the first layer with the substrate and the second layer. For example, when the first layer is a nitride compound, surface reactions can produce a thin layer of oxide, i.e., an oxynitride. The oxynitride formed at the interface of the first and second layers can promote wetting and diffusion into the second layer components during the sintering process, thus effectively producing another interlayer. The bonds produced by chemical diffusion (i.e., metallurgical bonds) are very strong, resulting in interface having very high bond strengths.

The second layer comprises an a binder that is insoluble in body fluids and a apatite. The apatite in the second layer of the coating is a bio-compatible apatite, preferably selected from the group consisting of hydroxyapatite $Ca_{10}(PO_4)_6(OH)_2$, fluorapatite $Ca_{10}(PO_4)_6F_2$, hydroxyfluorapatite $Ca_{10}(PO_4)_6(OH)_{2-x}F_x (x<1)$, and the like. The preferred coating material is hydroxyapatite for metallic hip, knee, spine and other orthopedic implants, while fluorapatite and hydroxyfluorapatite are favorable for coating dental implants.

It is contemplated that the apatite in the second layer will have high crystallinity to minimize coating dissolution problems. By high crystallinity, it is meant equal to or greater than about 90% crystallinity, with equal to or greater than about 95% crystallinity preferred, and equal to or greater than about 98% crystallinity more preferred. Crystalline apatites are relatively insoluble in body fluid under in vivo conditions. Amorphous apatites and other calcium phosphates are soluble in body fluids. Without being held to theory, it is believed that the crystalline apatites will not substantially dissolve in body fluid thus keeping the thickness of the coating substantially the same during implant service and improve the implant long-term viability.

Similarly, the purity of the apatite in the second layer is greater than or equal to about 90%, preferably greater than or equal to about 95%, more preferably greater than or equal to about 98%, and most preferably greater than or equal to about 99%. High crystallinity and purity can be produced by treating the starting apatite powder in an autoclave at high pressure and temperature, resulting in a highly crystallized apatite. Alternatively, the raw material of the apatite can be derived from a liquid chemical reaction, wherein the composition is controlled using a high purity raw material and high pH conditions, under which only the apatite phase is stable, and other soluble materials such as tricalcium phosphate and tetracalcium phosphate can be removed from the solution. The crystallinity and purity can be maintained by low temperature sintering in the presence of a binder. The sintering temperature of the apatite-glass coatings is below about 950° C. At this low sintering temperature, the apatite has very high stability, i.e., little apatite will convert to the amorphous phase or decompose. In addition, the binder melts resulting in encapsulation of the apatite particles, greatly inhibiting apatite decomposition.

The apatite can have micrometer (greater than 0.1 micrometer to a maximum of about 100 micrometers) or nanometer (less than about 100 nanometers) grain sizes. To maximize the bioactivity, nanometer grained apatite (nano-apatite) is preferred in this layer. By nanostructured or nanometer grained apatite, it is meant apatite having maximum grain sizes of about 100 nanometers.

Figure 3:
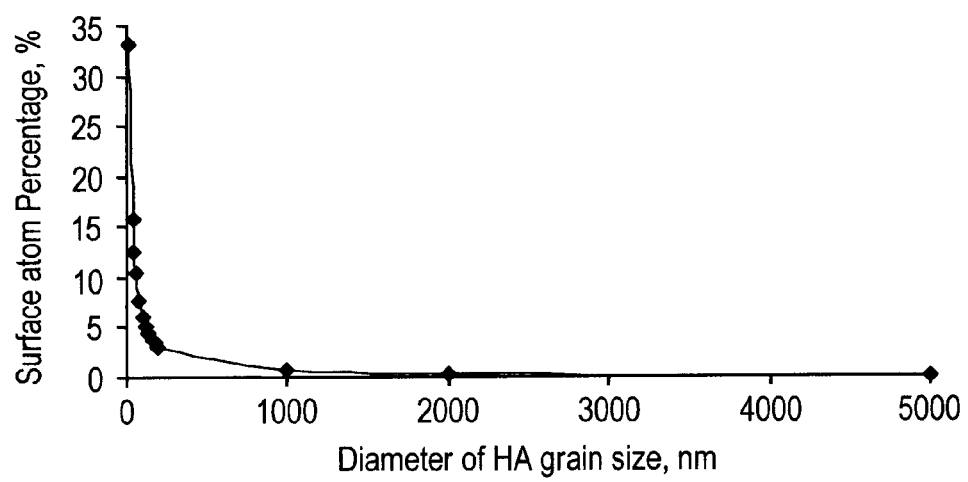
FIG. 3 shows a schematic illustration of the volume percentage increase of surface atoms as a function of decreasing apatite grain size, where the grain has a spherical shape with an assumed surface layer 1.0 nm in thickness.

There are several advantages to using apatite having nanometer sized grains. First, the nanometer sized apatite grains have a higher percentage of surface area to volume than larger particles and thus a higher percentage of atoms at the surface. For nanometer grained hydroxyapatite (nano-HA), the percentage of atoms at the surface is 6% for a grain size of 100 nm, which is 100 times higher than the percentage of atoms at the surface (0.06%) for 10.0 micrometer (μm) hydroxyapatite grains, as shown in FIG. 3. In addition, if the hydroxyapatite grain size goes down to 2 nanometer (nm), up to about 100% of the atoms will reside on the surface and thus at the grain boundaries. Without being held to theory, it is believed the higher the percentage of atoms at the apatite coating surface, the greater will be the new biological apatite deposition from body fluid. Significant increases in biological apatite deposition can assist in new bone growth and other tissue growth onto and into the coating. Bone and tissue growth into the coating can improve the fixation at the coating-tissue interface.

A second advantage is that use of nanometer sized apatite grains strengthens the apatite-binder composite itself. The nanometer sized apatite grains have a dispersion strengthening effect for the composite coating, which makes the coating itself stronger. This dispersion strengthening mechanism of nanometer sized grains has long been recognized in the steel, ceramic, and rubber industries. The coatings disclosed herein use the same strengthening mechanism for biomedical materials.

Third, the use of nanometer sized apatite grains aids in early fixation of implants, in that the higher the number of surface atoms of apatite, the quicker the healing at the site of implantation. This earlier fixation decreases the implant micromotion, consequently decreasing the migration of wear debris particles into the coating/implant interface area. Earlier fixation also contributes to the long service life of the implants.

The second layer also comprises a binder that is insoluble in body fluids. It is also preferred that the binder be inert in biological samples. In the case of a glass material, inert as used herein means a glass that does not react with body fluids or body tissue. A preferred insoluble material is a glass, such as, for example, a borosilicate glass with good stability in neutral solution, such as those used in medical devices such as syringes. The preferred glass composition comprises about 67.8 wt % to about 80 wt % $SiO_2$, about 4 wt % to about 6 wt % $Al_2O_3$, about 6 wt % to about 12 wt % $B_2O_3$, about 8wt % to about 15 wt % ($Na_2O$, $K_2O$, and $Li_2O$), about 0.5 wt % to about 3.0 wt % ($ZrO_2+TiO_2$), and about 0.5 wt % to about 4.0 wt % (BaO, ZnO, MgO, and CaO) based on the total weight of the glass. Preferred glasses have a thermal expansion coefficient of about $4.0$–$8.0 \times 10^{-6}/°$ C. The preferred composition of the glass is elaborated in detail below.

The $SiO_2$ forms the basic network of the glass, giving the glass a uniform structure. If the $SiO_2$ content is less than about 67.8 wt %, the glass can have a thermal expansion coefficient too high to adjust the thermal expansion coefficient of the second layer to be similar to that of the first layer and the metal substrate. When the thermal expansion coefficient of the second layer is significantly different from the first layer (i.e., more than about $1.0 \times 10^{-6}/°$ C. different), the coating can separate from the metal substrate. In addition when the $SiO_2$ content is larger than about 80 wt %, the glass can have a thermal expansion coefficient too low to adjust thermal expansion coefficient of the second layer to be similar to that of the metal substrate or first layer.

The $Al_2O_3$ can minimize the phase separation of the borosilicate glass. Without being held to theory, it is believed that the $Al_2O_3$ makes the glass more stable in body fluid. If the $Al_2O_3$ content is less than about 4 wt %, the chemical stability of the glass can be too low for the glass to be melted. If the $Al_2O_3$ content is higher than about 6 wt %, the chemical stability of the glass can be too low, i.e., in body fluid at 37° C. Also, the melting point and viscosity of the glass at high temperature can be too high, leading to a second layer that is difficult to sinter.

$B_2O_3$ can form another basic network of the glass, decreasing the melting point of the glass, and making the glass more stable (i.e. acting as an anti-crystallization agent). If the $B_2O_3$ content is less than about 6 wt %, the borosilicate glass has high melting point and can be relatively easily to crystallize. If the $B_2O_3$ content is higher than about 12 wt %, the borosilicate glass can separate into a two-phase glass (i.e., a borate glass and a silicate glass). Both glass phase separation and crystallization can result in low chemical stability of the glass in body fluid.

The $Na_2O$, $K_2O$, and $Li_2O$ can supply bridged oxygen between the $SiO_2$ and $B_2O_3$ networks. If the ($Na_2O$, $K_2O$, and $Li_2O$) content is less than about 8 wt %, there may not be enough bridged oxygen to bond the two networks. The viscosity of the glass can be too high for the glass to be melted. If the ($Na_2O$, $K_2O$, and $Li_2O$) content is higher than about 15 wt %, the two networks can easily break down, leading to a readily crystallizable glass. At greater than about 8 wt % to about 12 wt % of ($Na_2O$, $K_2O$, and $Li_2O$), the chemical stability of the glass body in fluid can be decreased thus rendering the glass unsuitable for medical coating applications.

BaO, ZnO, MgO and CaO can be used in addition to, or in place of, at least part of the $Na_2O$ to increase the chemical stability of the glass in body fluid. The preferred amount of these compounds is about 0.5 wt % to about 4 wt %. If the content is more than about 4.0 wt %, the glass can either become more brittle and sensitive to melting process, or more porous.

A small amount of $ZrO_2$ and $TiO_2$ (about 0.5 wt % to about 3.0 wt %) can increase the chemical stability of the borosilicate glass in human body fluid, but a large amount of the $ZrO_2$ and $TiO_2$ (i.e., greater than about 3.0 wt %) can cause glass crystallization.

Without being held to theory, it is believed that adding glass to the second layer allows the adjustment of the thermal expansion coefficient of the coating. The apatite-binder layer thermal expansion coefficient $\alpha$ can be described by equation (6), where $W_h$, and $W_g$ stand for the volume fractions of apatite and glass, $\alpha_h$ and $\alpha_g$ represent the thermal expansion coefficients of apatite and glass, respectively, and where a and b are constants. The thermal expansion coefficient of, for example, hydroxyapatite ($13.3\times 10^{-6}/°$ C.) is larger than that for Ti and Ti6Al4V implants ($9.6\times 10^{-6}/°$ C. for titanium and $10.3\times 10^{-6}/°$ C. for Ti6Al4V). A lower $\alpha_g$ can be selected to match the composite coating $\alpha$ as close as possible to the metal implant or first layer $\alpha$. If the thermal expansion coefficient difference is less than about $1.0\times 10^{-6}/°$ C., the second layer should not crack when the coating thickness is less than about 100 micrometers.

$$\alpha = aW_h\alpha_h + bW_g\alpha_g \quad (6)$$

The thermal expansion coefficient of stainless steel implants is $14–17\times 10^{-6}/°$ C., much higher than that of hydroxyapatite. To adapt the thermal expansion coefficient of a stainless steel or CoCr alloy implant to accommodate the second layer, an intermediate Ti, Ti6Al4V, $Al_2O_3$, TiN, or other layer can be applied on the stainless steel or CoCr alloy. Thus, the coefficient of thermal expansion of the second layer can be matched to the substrate or to a coating on the substrate including, for example, the dense or first layer disclosed herein. The coefficient for TiN is $9.6\times 10^{-6}/°$ C., which is very close to that of Ti6Al4V. When the coating on the substrate and the second layer have similar thermal expansion coefficients, the coefficient of thermal expansion mismatch is minimized.

Another advantage of introducing glass into the second layer is that the sintering temperature of the layer can be adjusted to be lower than phase transformation temperatures of Ti, Ti6Al4V, stainless steel, and CoCrMo, and the like. A typical metallic materials phase has a transformation temperature of about 975° C. Below 975° C., the mechanical properties of the metals can be maintained. Above 975° C., the mechanical properties of the metals can be damaged. Also, stoichiometric hydroxyapatite is stable in air and in vacuum at temperatures less than about 1,000° C. However, apatite, especially hydroxyapatite, has a sintering temperature over 1,000° C., typically 1,100–1,300° C. In order to lower the sintering temperatures of the second layer, the binder, i.e., glass, is introduced into the second layer. Glass becomes soft in a relatively low temperature range (500–975° C.). The amount of glass added and the composition of the glass can be adjusted to make low-temperature sintering (less than or equal to about 975° C.) available.

The advantages of low temperature sintering are maintaining apatite crystallinity, maintaining apatite purity, and maintaining apatite grain size. The high crystallinity and purity can result from two factors, the raw material and sintering process. High temperature sintering (i.e., greater than about 1,000° C.) can result in the production of amorphous phase apatite and thus decomposition of the apatite in body fluids. At low temperatures (i.e., less than about 975° C.), the apatite can have very high stability in the crystalline phase, i.e., the apatite will not transfer to amorphous phase and decompose. In addition, upon sintering the glass will melt and encapsulate the nanograined apatite particles, potentially inhibiting apatite decomposition in a low water vapor atmosphere.

Another advantage of using glass in the second layer is the reduction of cracking during and after sintering. Zhiitomirsky L. Gal-OR in "Electrophoretic Deposition of Hydroxyapatite," *J. Mater. Sci. Med.* 8: 213–219, 1997 reported that cracks were generated in a direction parallel to the implant surface, due to shrinkage from sintering. By incorporating glass into the second layer, it is hypothesized that the sintering of apatite and glass composites is liquid sintering, i.e., the sintering shrinkage is through liquid glass deformation, instead of apatite shrinkage. Sintering shrinkage through liquid glass deformation rather than apatite shrinkage can lead to reduced cracking of the second layer.

Another advantage of utilizing glass in the second layer is to increase the coating bond strength. The glass will act as a binder. Thus the glass not only bonds apatite particles inside of the second layer, but it also adheres the first layer to the second layer. Furthermore, the apatite-glass composites can be sintered at temperatures below 975° C., thus reducing the formation of amorphous apatite and other dissolvable calcium phosphates. Therefore, the second layer is stable in body fluid, and consequently can retain the bond strength for long-term service in vivo.

In the second layer, the apatite comprises about 51 wt % to about 80 wt % and the binder, insoluble in body fluids, (i.e., glass), comprises about 20 wt % to about 49 wt % based on the total weight of the second layer. The preferred composition is 60 wt % to 65 wt % apatite and 35 wt % to 40 wt % binder. If the apatite content is less than about 51 wt %, the coating bond strength is high (64 MPa), but the bioactivity is low. If the apatite content is higher than about 80 wt %, the bioactivity is high but the bond strength is low (17 MPa, similar to a conventionally thermal sprayed hydroxyapatite coating).

Within the second layer, the distribution of the apatite can be can be either uniform or vary via a concentration gradient. By a concentration gradient, it is meant that the concentration varies from a high value to a lower value, or from a low value to a higher value in a direction perpendicular to the implant. The term gradient is not meant to imply that the concentration varies uniformly, although this is a possibility. The preferred distribution is a higher weight percentage of apatite near the tissue interface (i.e., about 100%), and a lower weight percentage of apatite near to the first layer-second layer interface (i.e., about 1 to about 30 wt %). In this embodiment, the thermal expansion coefficient of the second layer gradually changes from one interface to the other, thus decreasing residual thermal stress. The proportion of apatite to glass in the second layer coating is also dependent on the first layer. For Ti or Ti6Al4V implants, the second layer coating containing less apatite and more glass is preferred. For stainless steel and CoCrMo prostheses, more apatite and less glass are suitable.

The preferred thickness for the second layer is about 5 micrometers to about 100 micrometers. In general, if the apatite-glass layer is less than about 5 micrometers thick, the coating may not be thick enough to supply bioactivity, whereas if the apatite-glass layer is thicker than 100 micrometers, the coating may not supply additional bioactivity and will have a higher cost.

The multi-layer coating optionally comprises a third layer disposed on and preferably in contact with the second surface of the second layer. The third layer preferably comprises an apatite. In contrast to the second layer, however, the apatite in the third layer is preferably less than about 90%, more preferably less than about 80%, and most preferably less than about 70% crystalline. The lower crystallinity in the third layer as compared to the second layer can facilitate the integration of the implant into the surrounding tissue.

The third layer can optionally comprise a physiologically active agent. Alternatively, the second layer may be coated, it brush coated, with a physiologically active agent. As used herein, an active agent refers to an agent that has a physiological activity such as a diagnostic or therapeutic activity. Accordingly, an active agent can include a detectable label (e.g., a radioactive label) that is useful for identifying the locations of the released agent in vivo. Active agents also include therapeutic agents which are useful for treating a disease or condition. The categories of physiologically active agents which can be used in the third layer include, but are not limited to, antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, and so on. The active agents can be, for example, protein or peptide agents, nucleic acids such as DNA, RNA and PNA, and drugs.

Exemplary antibiotics include tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Exemplary anti-tumoral agents include doxorubicin, Daunorubicin, taxol, methotrexate, and the like. Exemplary antipyretics and analgesics include aspirin, Motrin, Ibuprofin, naprosyn, Indocin, acetaminophen, and the like.

Exemplary anti-inflammatory agents include NSAIDS, aspirin, steroids, dexamethasone, hydrocortisone, prednisolone, Diclofenac Na, and the like.

Exemplary therapeutic agents for treating osteoporosis and other factors acting on bone and skeleton include calcium, alendronate, bone GLa peptide, parathyroid hormone and its active fragments, histone H4-related bone formation and proliferation peptide and mutations, derivatives and analogs thereof.

Exemplary enzymes and enzyme cofactors include pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Exemplary cytokines include transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example TGF-beta 1, TGF-beta 2, TGF-beta 3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Exemplary anticoagulants include warfarin, heparin, Hirudin, and the like.

Exemplary factors acting on the immune system include factors which control inflammation and malignant neoplasms and factors which attack infective microorganisms, such as chemotactic peptides and bradykinins.

The physiologically active agent can also be a cell. Mesenchymal stem cells, for example, can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; etc. The cells may be either allogeneic or xenogeneic in origin. For example, the cells can be from a species other than the host species that have been genetically modified.

Physiologically active agents may be incorporated into the third layer by admixture. Alternatively, the agents may be incorporated into the third layer by binding these agents to the functional groups on synthetic polymers. Processes for covalently binding physiologically active agents such as growth factors using functionally activated polyethylene glycols are described in U.S. Pat. No. 5,162,430. Such compositions can include linkages that can be easily biodegraded, for example as a result of enzymatic degradation, resulting in the release of the active agent into the target tissue, where it will exert its desired therapeutic effect.

Alternatively, the physiologically active agent can be added to the third layer in a controlled released formulation. One form of controlled release formulation contains the active agent dispersed or encapsulated in a slowly degrading, non-toxic, non-antigenic polymer such as copoly(lactic/glycolic) acid, as described in the pioneering work of Kent, Lewis, Sanders, and Tice, U.S. Pat. No. 4,675,189. Suitable biodegradable polymers include, for example, polylactic acid (PLA) and copoly(lactic/glycolic) acid (PLGA). The active agents may also be formulated in cholesterol or other lipid matrix pellets, or silastomer matrix implants. Additional slow release formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987.

The active agent may be delivered along with various other agents as required in the particular instance. The formulation of pharmaceutically-acceptable excipients and carrier solutions are well-known to those of skill in the art. The term "effective amount" refers to the amount of active agent required in order to obtain the effect desired. Thus, a "tissue growth-promoting amount" of a composition refers to the amount needed in order to stimulate tissue growth to a detectable degree. Tissue, in this context, includes connective tissue, bone, cartilage, and other tissues. The actual amount that is determined to be an effective amount will vary depending on factors such as the size, condition, sex and age of the patient and can be readily determined by one of skill in the art.

In another embodiment, a substrate or implant coated with the first and second layers as well as the optional third layer is provided. The substrate can comprise an orthopedic or dental prosthesis or implant. The substrate is preferably a metallic substrate. Implant includes, for example, substitutes, prosthetics, reinforcements etc, for hard tissues such as teeth, artificial roots of teeth, artificial bones, bone plates, and the like. The implant can be, for example, an artificial hip, knee, spine, ankle, finger, hand, leg, and the like. Suitable materials for the substrate include, for example, metals such as Ti, Ti6Al4V, CrCoMo, stainless steel, and the like; and ceramic materials. The substrate surface can have a certain porosity and roughness. If necessary, porosity and roughness can be increased by means of appropriate treatments, such as, for example, laser treatment, sanding, plasma-spraying, and the like. The surface roughness can be about 10 to about 500 micrometers, although surface roughness is not critical.

In another embodiment, a method of coating an implant is provided. The multi-layer coatings can be fabricated onto a metallic substrate by depositing the first layer on the surface of metallic implants, depositing an apatite and binder composite to form a green coating and sintering the green coating at a temperature below about 975° C.

The substrate can be, for example, Ti, Ti6Al4V, stainless steel 316, or ASTM F75 CoCrMo alloy. The sample can optionally be sandblasted prior to deposition of the first layer.

As described in detail above, the first layer can comprise oxide compounds, nitride compounds, boride compounds and carbide compounds. The deposition method for the first layer is at least somewhat dependent on the subsequent deposition method for the apatite-binder composite. Suitable first layer deposition methods include, for example, plasma spray, baking, thermal decomposition, sputtering, chemical vapor deposition (CVD), anolization, physical vapor deposition (PVD), and the like. For oxide compounds, chemical vapor deposition and anolization are preferred when the apatite-binder composite will subsequently be deposited by non-electrical methods such as, for example, air spray, dip coating, brush coating, and the like. For nitride, boride and carbide compounds, CVD and PVD are preferred when the apatite-binder composition will be applied by electrical methods such as, for example, electrophoretic deposition.

The apatite and binder composite green coating is formed by depositing at least one slurry comprising the apatite, the binder, and a solvent on the first layer. The solvent is selected from water and organic solvents, preferably a polar organic solvent, for example, alcohols comprising 1 to about 4 carbons. The preferred apatite is nanometer grained apatite. Autoclave treated hydroxyapatite ($Ca_{10}(PO_4)_6(OH)_2$) particles with a grain size less than about 40 nanometers and about 100% crystallinity are available from Berkeley Biomaterials, Inc., CA. Other nanometer grained hydroxyapatite materials from Alfar Aesar Inc., MA and by an Inframat internal process can also be used. Other nanograined apatites prepared by chemical precipitation and autoclave can be used, such as fluorapatite $Ca_{10}(PO_4)_6F_2$, hydroxyfluorapatite $Ca_{10}(PO_4)_6(OH)_{2-x}F_x (x<1)$, and the like. The slurry can comprise about 30 wt % to about 100 wt % of apatite. The particle size of the binder is dependent upon the coating method to be used. For example, for electrophoretic deposition, the preferred initial binder particle size is less than or equal to about 10 micrometers. For brush application, the preferred initial particle size is less than or equal to about 50 micrometers. Glass powder with a particle size of about 1 micrometer is available from Corning Glass Co. The glass composition can be $SiO_2$ 67.8–75 weight percent (wt %), $Al_2O_3$ 4–6 wt %, $B_2O_3$ 6–12 wt %, ($Na_2O+K_2O+Li_2O$) 8–15 wt %, ($ZrO_2+TiO_2$) 0.5–3.0 wt %, and (BaO+ZnO+MgO+CaO) 0.5–4.0 wt %, based on the total weight of the glass. Before dispersion, the glass can be reduced to submicron size using a high-energy ball-milling technique for about 3 to about 72 hours.

The powder content in the slurry can be from 5–20 weight percent (wt %) based on the weight of the slurry. Slurries can be made that contain different apatite concentrations, such as, 30 wt %, 40 wt %, 50 wt %, 55 wt % 60 wt %, 70 wt %, 80 wt %, and 100 wt % apatite particles, based on the combined weight of hydroxyapatite and glass.

The slurry can be coated onto the first layer using, for example air spray, dip coating, brush coating, or electrophoretic deposition (EPD). Deposition can be performed with an anode comprising, for example, platinum or graphite, and a cathode comprising the metallic substrate coated with the dense layer. The distance between the electrodes can be about 5 to about 25 centimeters. EPD can be conducted, for example, as an electroplating process.

The preferred green coating comprises a concentration gradient of apatite in the binder. The gradient can be formed, for example, by layering slurries comprising increasing concentrations of apatite onto the dense layer coated substrate. A plurality of slurries can be formed and then layered such that each successive layer has a higher concentration of apatite than the previous layer. The coating thickness for deposition of each slurry can be controlled by varying the voltage and the time (using conductive methods) or time alone (using non-conductive methods). Preferably, the concentration of apatite in the slurry layered nearest the first layer is about 30 wt % and about 100 wt % apatite in the slurry layered farthest away from the first layer. Once coated, the slurry can be dried at ambient temperature or in an oven at a temperatures of 10° C. to 200° C.

The green coating is sintered at temperatures below about 975° C. Sintering can, for example, be performed as a two-step process comprising oxidation and sintering. Oxidation can be performed, for example, at temperatures of about 500° C. to about 800° C. for a time sufficient to form an oxygen containing layer, typically about 30 to about 120 minutes under an atmosphere comprising oxygen. Sintering can then be performed at temperatures of about 850° C. to about 975° C. for 5 to 30 minutes in, for example, a nitrogen atmosphere. Alternatively, sintering can comprise heating at a temperature of about 500° C. to less than about 975° C. for about 5 to about 240 minutes in a vacuum, nitrogen, argon, helium, or other inert atmosphere. The heating rate can be controlled, for example, at 10° C./min in the pre-oxidation step and 20° C. in the sintering step.

The optional third layer can be deposited after sintering of the first and second layers to prevent decomposition of any added physiologically active agents. The third layer is preferably deposited by such techniques as air spray, dip coating, brush coating, or electrophoretic deposition (EPD). After deposition, the third layer can be dried.

The invention is further illustrated by the following non-limiting examples:

EXAMPLES

Example 1

The substrate was Ti6Al4V purchased from Prudential Titanium Inc., MA. The metallic substrate with a dimension of 1.0 inch in diameter by 0.125 inches thick was sandblasted. This sample was coated with a first layer of TiN using a PVD process at Ionbond Inc., NJ. The first layer had a thickness of about 4 micrometers.

The second layer contained stable silicate glass and nanometer grained hydroxyapatite powder. The silicate glass was composed of 67.80 wt % $SiO_2$, 10.30 wt % $B_2O_3$, 8.30 wt % $Na_2O$, 5.20 wt % $Al_2O_3$, 4.20 wt % $K_2O$, 2.10 wt % $LiO_2$, 1.05 wt % $ZrO_2$, and 1.05 wt % $TiO_2$. The glass was milled into a powder with a particle size less than about 1.0 micrometer. The glass powder was stable in hot water and had a thermal expansion coefficient of $7.8 \times 10^{-6}/°C$. The nanometer grained hydroxyapatite was synthesized by the Inframat Corporation using chemical precipitation and autoclave treatment. The hydroxyapatite had a particle size of about 30–50 nanometer. Hydroxyapatite particles, medical glass particles, and 2-propanol were mixed by ball milling into a slurry. The slurry had a solids content of 10 wt %.

Electrophoretic deposition (EPD) was conducted to form the nanometer grained hydroxyapatite composite green coating. During the EPD process, the anode was platinum, which was inert during the deposition. The cathode was the TiN coated Ti6Al4V substrate. The distance of the electrodes was 10 centimeter. The electrophoretic deposition was conducted at 5V for 5 minutes for each composition. The EPD was sequentially conducted with a 30 wt % nanometer grained hydroxyapatite slurry, a 50 wt % nanometer grained hydroxyapatite slurry, a 60 wt % nanometer grained hydroxyapatite slurry, an 80 wt % nanometer grained hydroxyapatite slurry, and a 100 wt % nanometer grained hydroxyapatite slurry. The EPD process was finished when the total composite green coating thickness reached about 30 micrometers. The green coating was dried at 50° C. in an oven overnight.

The sintering was divided into two stages. The first stage was heating at 600° C. for 30 minutes in a mixture of dry air and to oxidize TiN surface. The oxidized substrate can increase wetting ability of glass to the substrate. The second stage was sintering at 950° C. for 30 minutes to densify the coating.

Example 2

The substrate was Ti purchased from Prudential Titanium Inc., MA. The metallic substrate with a dimension of 1.0 inch in diameter by 0.125 inches thick was sandblasted. This sample was coated with a first layer of TiN using the PVD process at Ionbond Inc., NJ. The first layer had a thickness of about 4 micrometers.

The second layer contained stable silicate glass and nanometer grained hydroxyapatite powder. The silicate glass was composed of 70.80 wt % $SiO_2$, 9.30 wt % $B_2O_3$, 8.30 wt % $Na_2O$, 5.20 wt % $Al_2O_3$, 2.20 wt % $K_2O$, 2.10 wt % $LiO_2$, 1.05 wt % $ZrO_2$, and 1.05 wt % $TiO_2$. The glass was milled into a powder with a particle size of less than about 1.0 micrometer. The glass powder was stable in hot water and had a thermal expansion coefficient of $6.6 \times 10^{-6}/°C$. The nanometer grained hydroxyapatite was synthesized by the Inframat Corporation using a chemical precipitation and autoclave treatment. The hydroxyapatite had a particle size of about 30–50 nanometers. Hydroxyapatite particles, medical glass particles, and 2-propanol were mixed by ball milling into a slurry. The slurry had a solids content of 50 wt %.

Electrophoretic deposition (EPD) was conducted to make the multi-layered nano-hydroxyapatite composite green coating. During the EPD process, the anode was platinum, which was inert during the deposition. The cathode was the TiN coated Ti6Al4V substrate. The distance between the electrodes was 8 centimeters. The electrophoretic deposition was conducted at 6V for 3 minutes for each composition. The EPD was sequentially conducted with a 40 wt % nanometer grained hydroxyapatite slurry, a 60 wt % nanometer grained hydroxyapatite slurry, a 70 wt % nanometer grained hydroxyapatite slurry, a 90 wt % nanometer grained hydroxyapatite slurry, and a 100 wt % nanometer grained hydroxyapatite slurry. The EPD process was finished when the total composite green coating thickness reached about 40 μm. The coated green coating was dried at 80° C. in an oven overnight.

The sintering was divided into two stages. The first stage was heating at 550° C. for 40 minutes in the mixture of dry air and to oxidize TiN surface. The oxidized substrate can increase wetting ability of glass to the substrate. The second stage was sintering at 970° C. for 60 minutes to densify the coating.

Comparative Example 1

Raw hydroxyapatite powder was purchased from Alpha Aesar, Inc. The raw hydroxyapatite powder was first sintered at 1300° C. for 2 hours to decrease the surface area. The sintered hydroxyapatite powder was crushed and attrition milled for 2 hours with water. The hydroxyapatite water slurry was spray dried into an agglomerated thermal stock with particle size of 40 to 60 micrometers.

The agglomerated powder was thermal sprayed onto a Ti6Al4V substrate (ASTM F136). The substrate was sandblasted using alumina granulates to roughen the surface prior to plasma thermal spraying. The parameters for plasma thermal spray were: secondary plasma gas hydrogen ($H_2$) with a flow rate of 2 liters/minute, spray current 600 Amperes, stand-off distance 7.5 centimeters, and coating thickness about 75 micrometers. The primary plasma gas was argon with a flow rate of 4 liters/minute. The carrier gas was argon with a flow rate of 3.2 liters/minute. The powder feed rate was 20 grams/minute, surface speed 7500 centimeters/minute, and transverse speed was 60 centimeters/minute.

Figure 9:
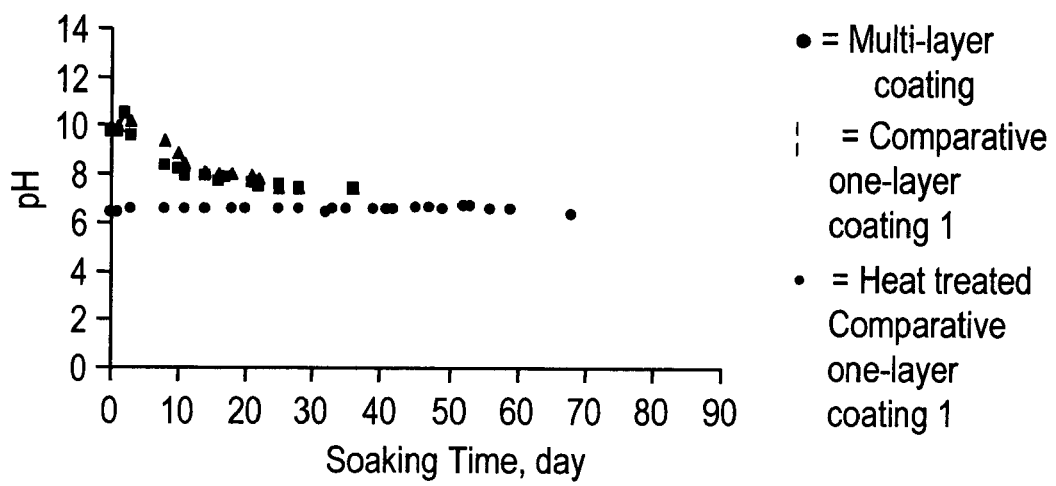
FIG. 9 shows the pH changes with soaking time in vitro for a multi-layer coating (●), as compared to a prior art one-layer hydroxyapatite coating (■, ▲).

In some cases, the coating of comparative example 1 was heat treated (see for example FIG. 9). The heat treatment was at 950° C. for 2 hours in argon. X-ray diffraction data showed that the heat treated hydroxyapatite coating by thermal spray had a crystallinity over 90% and another 10% of soluble calcium phosphates such as $Ca_3(PO_4)_2$ and CaO.

Comparative Example 2

Comparative Example 2 was chemically deposited according to the method of Yong et al., "Characterization and stability of hydroxyapatite coatings prepared by an electrodeposition and alkaline-treated process." *J. Biomed. Mater. Research.* 54:96–101, 2000.

Characterization of multi-layer coatings 1 and 2

The methods used to characterize the coatings are detailed below:

The extent and type of crystallization of the synthesized powder and coating layers were studied using X-ray diffraction (XRD). XRD analysis was performed using CuKα radiation with a scanning step of 0.02°/min and 2θ range of 10–60°. The grain size of the powder, D, was calculated according to the following equation $D = 0.89\lambda/[(W^2 - W_o^2)^{1/2} \cos\theta]$, where λ is the wavelength of X-ray beam (λ=0.154 nm for Cu $K_{\alpha 1}$ radiation), W is half-the width of XRD peaks at two theta angle (2θ) for the tested samples, and Wo is the half the width of the peak from standard samples, i.e.

conventional micrometer sized hydroxyapatite thermal spray feedstock powder, sintered at 1,300° C. for 2 hours in air.

The coating/metal substrate interfaces were examined and analyzed on polished cross sections using optical microscopy, and SEM with associated energy dispersive spectroscopy (EDS). EDS can be used to perform elemental analyses of the reaction layers and of the coating and alloy close to the interface. EDS analysis has a detection limit of about 1 wt % and a point-to-point resolution of about 1 micrometer.

Bond strength was measured according to ASTM Standard F 1147–99, "Standard Test Method for Tension Testing of Calcium Phosphate and Metallic Coatings."

For in vitro testing, an area 10×10 millimeters was soaked in 20 milliliters of simulated body fluid (SBF) at 37° C. for one month. The SBF composition is listed in Table 2. The solution was buffered at physiological pH 7.25 at 36.5° C. with 50 mM trishydroxyl aminomethane [$CH_2OH)_3CNH_2$] and 45 mM hydrochloric acid (HCl). After testing, the samples were removed from the liquid, rinsed in distilled water and dried with an air gun for further analyses. For comparison purposes, conventional thermal sprayed HA coatings were tested simultaneously using the same procedure.

TABLE 2

Composition of Hank's solution, (a simulated body fluid, 10 times concentrated without Calcium, Magnesium and Bicarbonate).

| Compounds | NaCl | KCl | Glucose | $KH_2PO_4$ | $NaH_2PO_4$ | Phenol red |
|---|---|---|---|---|---|---|
| Concentration | 80 g/L | 4 g/L | 10 g/L | 600 mg/L | 475 mg/L | 170 mg/L |

The corrosion of the multi-layer coating was tested in Hank's balanced salt solution obtained from Sigma Diagnostics, Inc. The Hank's solution was diluted 10 times using deionized water. Each coated Ti6Al4V sample was soaked in 20 ml diluted Hank's solution in a plastic beaker. To maintain the temperature, eight plastic beakers were positioned in a 12 inch×10 inch×20 inch water bath that was heated by electrical heaters. The temperature was automatically adjusted using a digital temperature controller (Fisher Scientific, Model 11-463-47 A). The pH of the Hank's solution containing the multi-layer coated sample was recorded by using a digital pH meter (Coming, pH-25). The calcium released from nanometer grained hydroxyapatite coating into the Hank's solution was measured by atomic absorption. Before the measurement, a series of standard calcium solutions were used for calibration. For the bond strength tests, 20 multi-layer coated samples were soaked in 400 milliliters Hank's solution at 37° C. Six samples were removed sequentially following each month of exposure in the corrosion test. For comparison, conventional thermal sprayed hydroxyapatite coatings were tested simultaneously using the same procedure.

Multi-layer samples were mounted on a sample holders using a 100% dense epoxy. The uncoated areas of the samples were sealed using epoxy, so that only the apatite-containing layer would be exposed to the Hank's solution during testing. The apatite-containing layer acted as working electrode, platinum as counter electrode, and calomel as reference electrode. The instrument used in the experiment was Potentiostat/Galvanostat, Princeton Applied Research, Model 173. The scanning range was −0.2–3.0 V with a speed of 0.02 V/minute.

Acidic etching was performed with a 3% HF (hydrogen fluoride) solution that was brushed on the polished surface of the multi-layer coating surface or on the polished cross-section surface of the multi-layer coating. After a 3 minute incubation, the 3% HF was washed 5 times using DI water.

The results of tests are described below.

Figure 4:
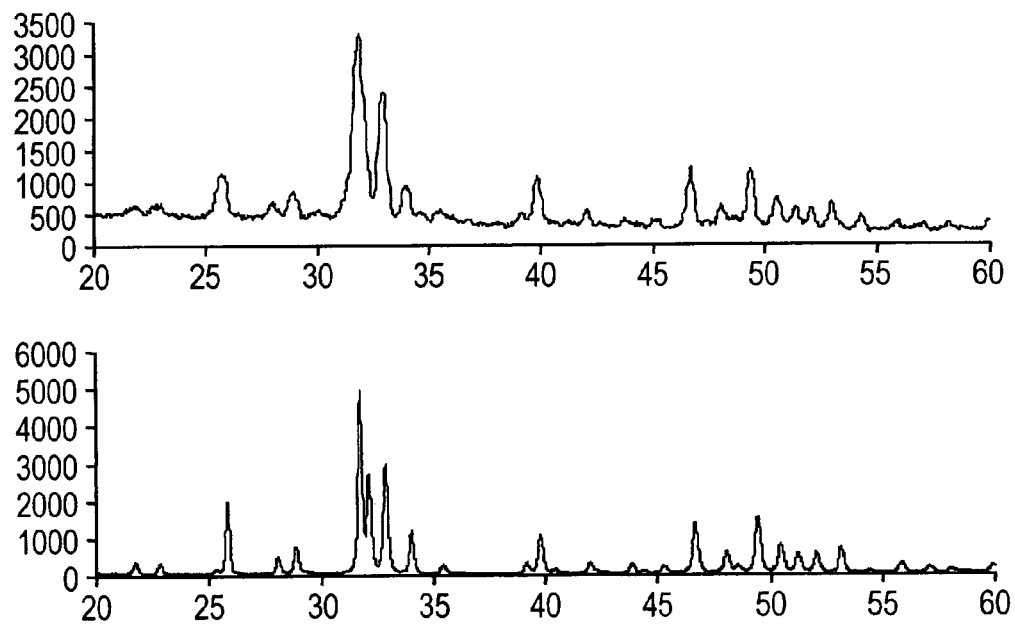
FIG. 4 shows X-ray diffraction (XRD) patterns of a sintered multi-layer coating comprising nanometer grained hydroxyapatite (Top panel), as compared to a prior art one-layer hydroxyapatite coating (Bottom panel).

FIG. 4 shows the XRD diffraction pattern of the surface of a multi-layer coating comprising hydroxyapatite with nanometer sized grains after sintering. XRD analysis revealed that the hydroxyapatite is a single crystalline phase located on the second layer. There is no amorphous hydroxyapatite or other calcium phosphate phases. The widened peaks of the hydroxyapatite indicated that the grain size of hydroxyapatite was about 60 nanometer (by the peak broadening calculation method). The crystallinity was measured by the integrated peak area and peak strength methods using ASTM standard D5357-98. Micrometer sized hydroxyapatite powders were sintered at 1300° C. for 2 hours as the standard samples. The results were:

(1). Relative crystallinity (peak strength ratio)=(690/662)×100%=104.23%

(2). Relative crystallinity (integrated area ratio)=(3260/3136)×100%=103.95%

The two methods generated essentially identical final results, this is, crystallinity at 104%, meaning that the derived crystallinity of the multi-layer coating comprising hydroxyapatite with nanometer sized grains is the same as the standard powder. The standard deviation of the test was 4%.

Figure 5:
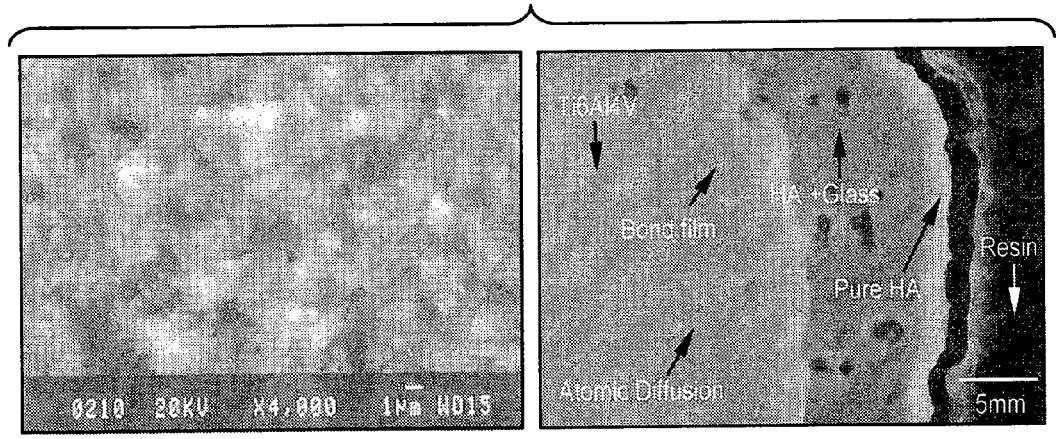
FIG. 5 shows scanning electron micrographs (SEM) of the surface structure of pure hydroxyapatite (Left panel) and the SEM cross-section structure of a multi-layer coating (Right panel).

FIG. 5 shows the surface structure (left panel) and cross-section structure (right panel) of a multi-layer coating comprising hydroxyapatite with nanometer sized grains. The hydroxyapatite had a well-developed crystalline nature and the uppermost surface of the coating exhibited several micron sized pores. Pure hydroxyapatite material with some pores would be beneficial for integration of new bone, or bonding with soft mammalian tissue. Also, there were layers on the Ti6Al4V substrate: a bond coating film and a nanometer grained hydroxyapatite gradient composite coating. This structure has the following features.

(1). All the layers appear very dense. The bond coating was a fully dense film. The nanometer grained hydroxyapatite gradient composite coating was dense with few isolated pores. The pure hydroxyapatite was located on the top surface.

(2). All the interfaces were tight without any cracks or pores.

(3). All the interfaces were chemically bonded via atom diffusion.

Figure 6:
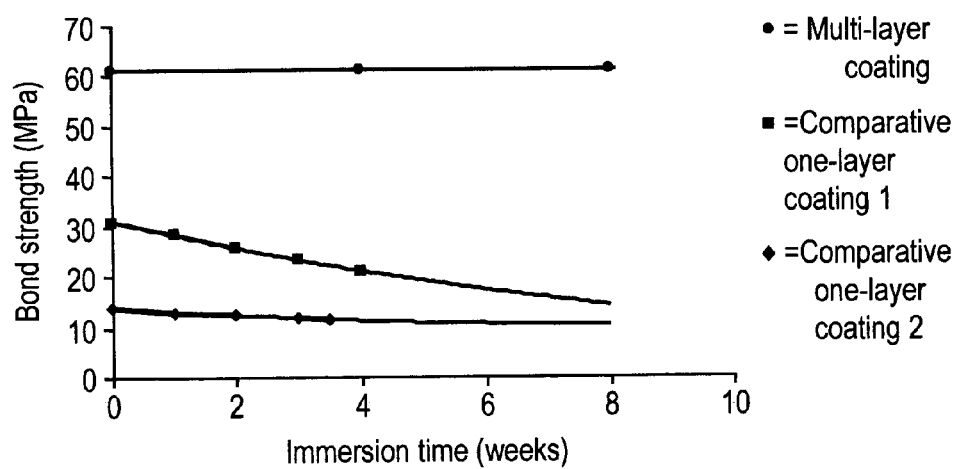
FIG. 6 shows a plot of bond strength vs. soaking time during in vitro testing in simulated body fluid of a multi-layer coating (●) and a prior art one-layer hydroxyapatite coating (■, ♦).

All measured bond strengths of the multi-layer coatings comprising hydroxyapatite with nanometer sized grains were greater than or equal to about 60 MPa (FIG. 6). The errors in the measurements were about 10% depending on the glue and curing procedures used. All tested multi-layer coating samples had failures in the glue, i.e., the bond strength of the coatings was higher than the glue bond strength of 60 MPa. This 60 MPa bond strength value exceeds the FDA required 50 MPa. The control one-layer coatings had bond strengths of 30 MPa or lower.

FIG. 6 also shows the bond strength as a function of soaking time in 37° C. simulated body fluid (SBF). The coatings of Examples 1 and 2 possessed a much higher initial tensile bond strength than one-layer hydroxyapatite coatings and chemically deposited one-layer hydroxyapatite coatings before in-vitro corrosion in simulated body fluid. During the in vitro testing period, e.g., 8 weeks, the bond strength of the multi-layer coatings retained a constant value (>60 MPa), but the one-layer coatings prepared by plasma spray suffered significant bond strength loss (25–30% loss in 4 weeks). The chemically precipitated one-layer hydroxyapatite coating had less bond strength loss, but the total strength was low.

Figure 7:
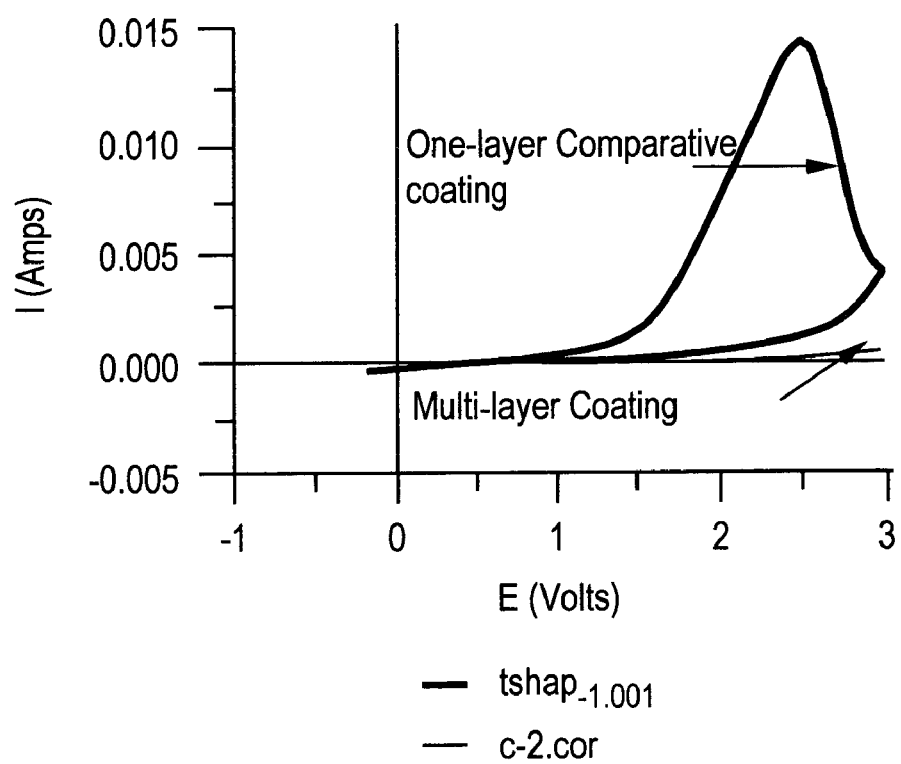
FIG. 7 shows the electropolarizing corrosion curve for a multi-layer coating comprising hydroxyapatite with nanometer sized grains, as compared to a prior art one-layer hydroxyapatite coating.

The corrosion resistance of the multi-layer coatings is shown in FIG. 7. The multi-layer coating corrosion in simulated body fluid was 300-fold less than that of a one-layer hydroxyapatite coating produced by thermal spray.

Figure 8:
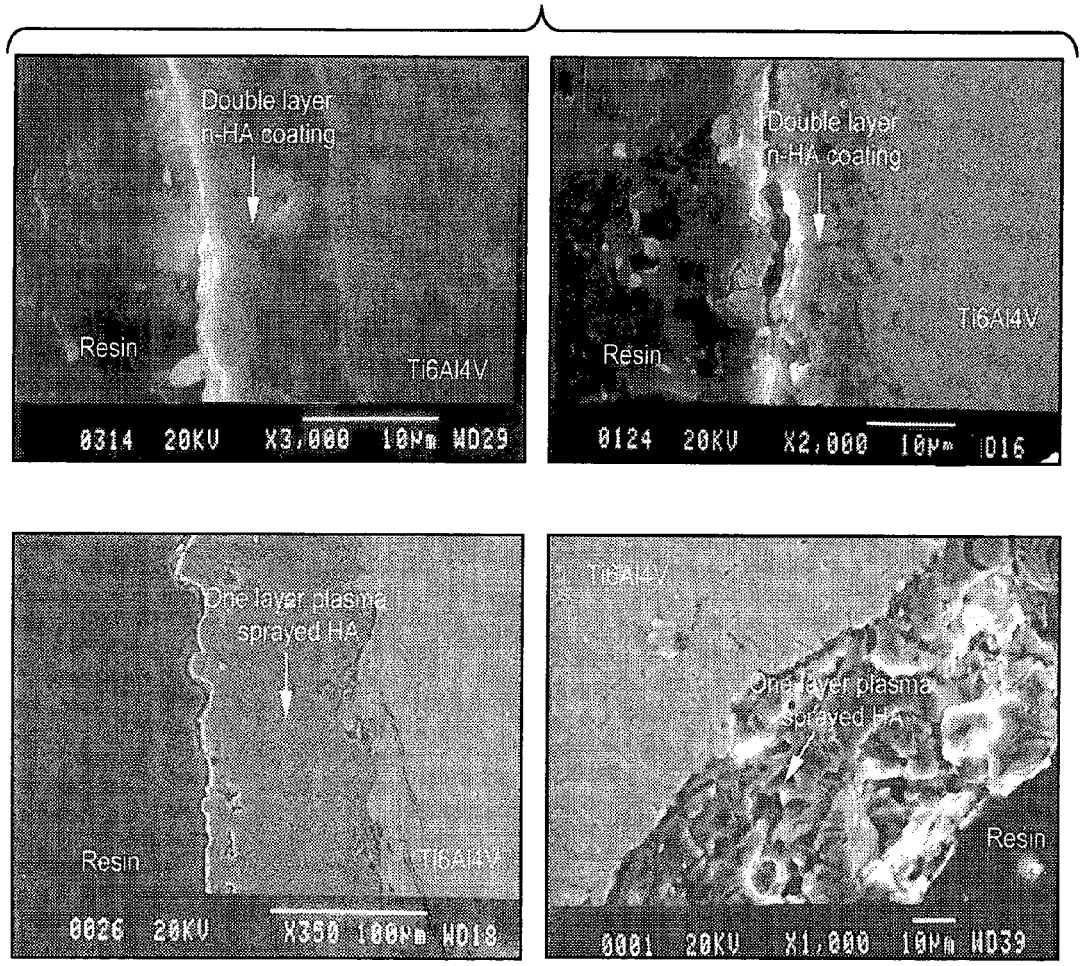
FIG. 8 shows SEM micrographs of the metal/coating interfacial structures of a multi-layer coating (Top panels) and a prior art one-layer hydroxyapatite coating (Bottom panels). The left pictures are before electropolarizing corrosion and HF etching, and the right pictures are after electropolarization corrosion with HF etching.

FIG. 8 shows SEM micrographs of the metal-coating interfacial structure of multi-layer coatings on a Ti6Al4V substrate before electropolarizing corrosion in simulated body fluid (FIG. 7, upper left) and after electropolarizing corrosion in simulated body fluid (FIG. 7, upper right). It is evident that both before and after electrical polarization, the multi-layered coating was bonded firmly to Ti6Al4V substrate. There is little change of the multi-layer coating/Ti interface. Comparatively, the thermal sprayed one-layer hydroxyapatite coating already had some cracks before electropolarizing corrosion (FIG. 7, lower left). After corrosion, the interface was totally separated, as shown in FIG. 8 (lower right).

FIG. 9 shows the pH change of the multi-layer coating with soaking time in simulated human body fluid at 37° C. For comparison, plasma sprayed one-layer hydroxyapatite coatings were also tested under identical conditions. It was found that a constant pH value at 6.5 was maintained with the multi-layer coating comprising hydroxyapatite with nanometer sized grains soaked in the simulated body fluid for more than 60 days. However, in the case of plasma sprayed one-layer hydroxyapatite coatings, the simulated body fluid exhibited a sudden pH increase up to 9.7. Two days later, the pH reached its highest value of 10.5. Thereafter, the pH gradually decreased to 7.5 and reached a stable value within 30 days. These curves demonstrate that the multi-layer coatings were much more stable than the conventional one-layer thermal sprayed hydroxyapatite coating during in vitro tests in the simulated body fluid.

Figure 10:
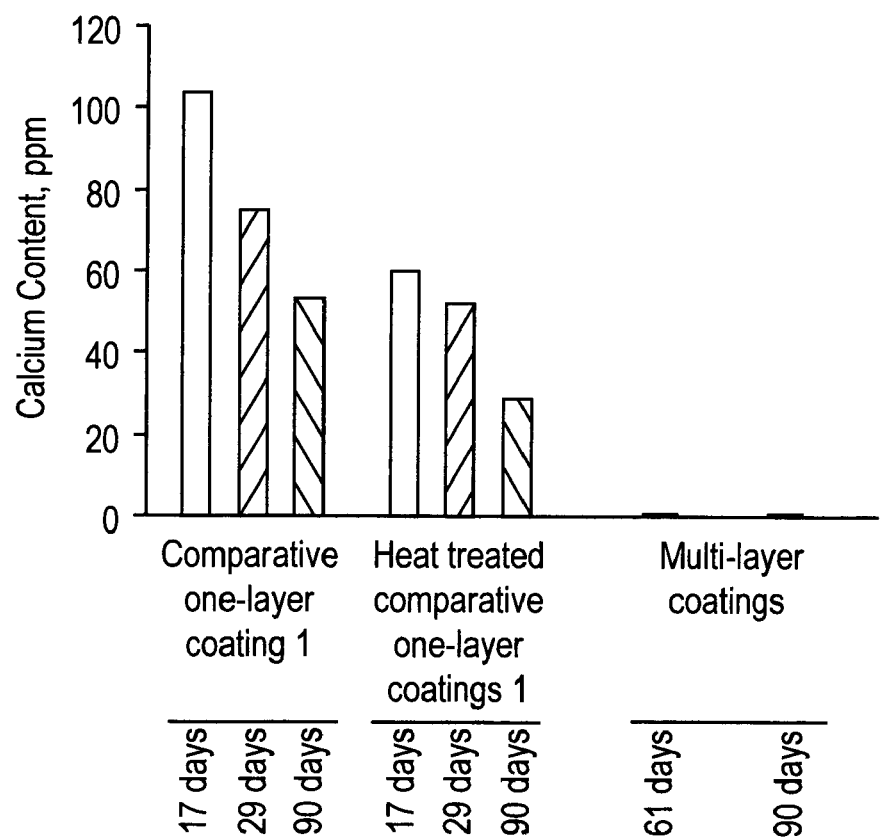
FIG. 10 shows the calcium content release into simulated body fluid for a multi-layer coating as compared with a prior art one-layer hydroxyapatite coating.

FIG. 10 shows the calcium content change with soaking time of both thermal sprayed ("T/S") one-layer hydroxyapatite coatings and the multi-layer coatings of examples 1 and 2. The calcium content release ranking can be expressed as:

Non-heat treated T/S HA coating>heat treated T/S HA coating>>multi-layered coating The two thermal sprayed one layer hydroxyapatite coatings both exhibited high calcium release, which was caused by the dissolution of amorphous hydroxyapatite and other calcium phosphate impurities in the coatings exposed to simulated body fluid. In contrast, the multi-layer coatings of examples 1 and 2, soaked 61 and 90 days, the calcium content in the simulated body fluid was zero, indicating no calcium release to the simulated body fluid.

Figure 11:
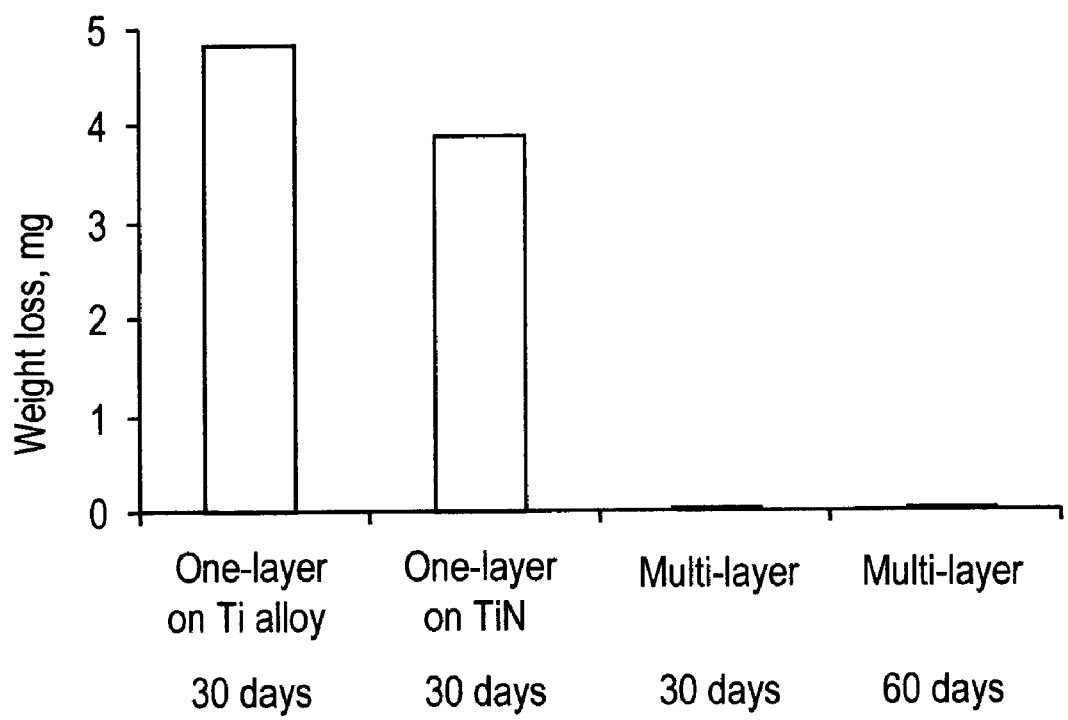
FIG. 11 shows the one month weight loss at 37° C. in simulated body fluid for a multi-layer coating compared to a prior art one-layer hydroxyapatite coating.

FIG. 11 shows the one month weight loss of the hydroxyapatite coatings in vitro at 37° C. The general trend was consistent with FIG. 10. The thermal sprayed one-layer hydroxyapatite coatings had a high weight loss during a one month soaking in simulated body fluid, while the multi-layer coatings exhibited no weight loss for the period tested.

Figure 12A:
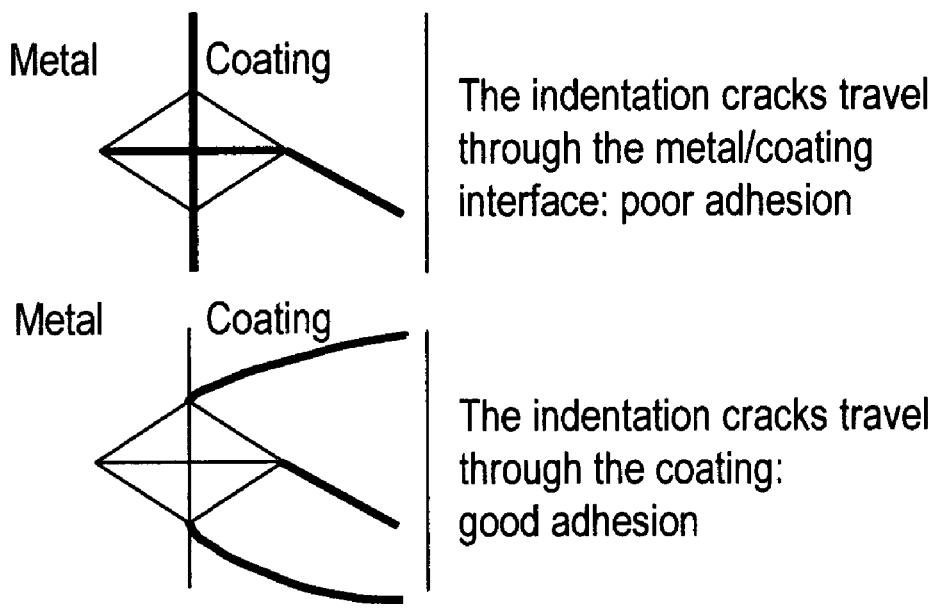
FIG. 12 shows (A) a schematic of the possible results of the crack resistance at the coating-implant interface and (B) the results for a multi-layer coating.
Figure 12B:
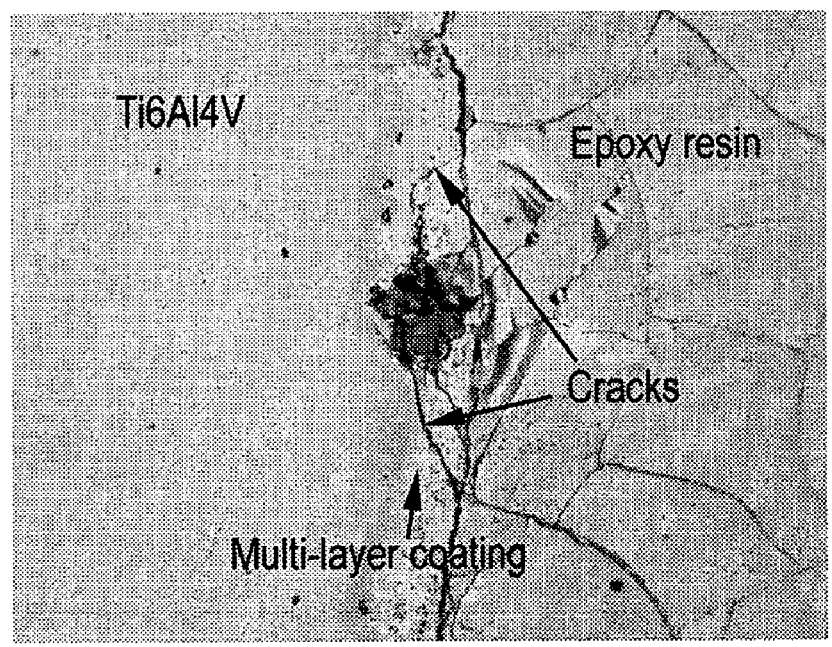

To study the adherence of the coatings, the relative crack resistance of the interface was qualitatively evaluated by indentation. A schematic of crack patterns is shown in FIG. 12A. When cracks travel across the interface, the coatings have poor adhesion. When the cracks travel through the coating, the coating has good adhesion. Indentations at the coating/metal interfaces were performed on polished cross sections (with a 1 micrometer Vickers pyramid diamond), using loads ranging from 0.05 to 1.2 kilograms in ambient air. As shown in FIG. 12B, the multi-layer coating exhibited cracks in the coating, not at the interface. The multi-layer coating thus exhibited good adhesion.

The multi-layer coating disclosed herein is particularly useful as a coating for metallic implants or prostheses. The first layer is a dense layer insoluble in body fluids, for example, TiN. The second layer comprises apatite and a binder that is insoluble and inert in body fluids. The apatite can be, for example, nanometer grained hydroxyapatite to facilitate the interaction of the second layer with the tissue. The binder can be, for example, glass comprising greater than 67.8% $SiO_2$. The multi-layer coatings preferably have no calcium release, no pH change and no weight loss when coated on a metal substrate and exposed to body fluid. The tensile strength of the coatings when applied to a metal substrate is preferably greater than or equal to about 60 MPa. Further, the corrosion current density is less than about $10^{-6}$ $mA/cm^2$. Implants coated with the disclosed multi-layered coating can be used as artificial bones, knees, screws, teeth, roots, spines and other types of orthopedic and dental materials.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A coating for an implant, comprising:
    a first layer comprising a material selected from the group consisting of nitride compounds, boride compounds, carbide compounds, and mixtures of two or more of the foregoing materials; and
    a second layer disposed on the first layer comprising hydroxyapatite and a glass, wherein the hydroxyapatite has a maximum grain size of about 100 nanometers and greater than about 90% crystallinity, and wherein the glass comprises about 67.8% to about 80%. $SiO_2$ based on the total weight of the glass.

2. The coating of claim 1, wherein the coating further comprises a third layer adjacent to the second layer, and wherein the third layer comprises hydroxyapatite.

3. The coating of claim 2, wherein the third layer further comprises a physiologically active agent.

4. The coating of claim 3, wherein the physiologically active agent comprises an agent selected from the group consisting of antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, cells, and combinations of two or more of the foregoing active agents.

5. The coating of claim 4, wherein the physiologically active agent comprises a controlled-release formulation.

6. The coating of claim 5, wherein the controlled release formulation comprises a biodegradable polymer.

7. The coating of claim 6, wherein the biodegradable polymer is selected from the group consisting of polylactic acid, copoly(lactic/glycolic) acid and combinations of two or more of the foregoing biodegradable polymers.

* * * * *